United States Patent [19]
Py

[11] Patent Number: 5,875,931
[45] Date of Patent: Mar. 2, 1999

[54] DOUBLE DISPENSER FOR MEDICINAL LIQUIDS

[76] Inventor: Daniel Py, 40, rue Franklin, 7800 Saint Germain En Laye, France

[21] Appl. No.: 661,246

[22] Filed: Jun. 10, 1996

[30] Foreign Application Priority Data

Jun. 14, 1995 [FR] France ................................. 95 07087

[51] Int. Cl.$^6$ .................................................. A61M 35/00
[52] U.S. Cl. .......................... 222/137; 222/162; 239/304; 239/307; 239/333
[58] Field of Search ..................... 222/137, 162, 222/340, 136; 614/82, 191, 294, 295, 298, 300, 301, 302; 239/303, 304, 307, 333

[56] References Cited

U.S. PATENT DOCUMENTS

| | | | |
|---|---|---|---|
| 3,178,118 | 4/1965 | New | 239/304 |
| 4,040,420 | 8/1977 | Speer | 604/82 |
| 4,605,398 | 8/1986 | Herrick | 604/300 |
| 4,623,337 | 11/1986 | Maurice | 604/298 |
| 4,739,906 | 4/1988 | LoTurco | 222/494 |
| 4,902,281 | 2/1990 | Avoy | 604/191 |
| 4,927,062 | 5/1990 | Walsh | 222/420 |
| 5,004,124 | 4/1991 | Stefaniak et al. | 222/136 |
| 5,024,355 | 6/1991 | Jouillat et al. | 222/162 |
| 5,190,190 | 3/1993 | Fudalla | 222/494 |
| 5,320,845 | 6/1994 | Py | 424/427 |
| 5,366,448 | 11/1994 | Basilice et al. | 604/302 |
| 5,578,019 | 11/1996 | Feldman | 604/295 |

FOREIGN PATENT DOCUMENTS 226 618  4/1990  New Zealand .

*Primary Examiner*—J. Casimer Jacyna
*Attorney, Agent, or Firm*—Kenyon & Kenyon

[57] ABSTRACT

A double-dispenser system for dispensing medicinal liquids has two jet-trigger pumps housed in an outer casing having at least one front opening and one rear opening. Each jet-trigger pump is provided with a dosing mechanism for dispensing a predetermined dose of medicinal liquid. Dispensation from the two pumps may be triggered simultaneously by a trigger device common to the two pumps and accessible from the outside of the casing. The pumps incorporated in the double-dispenser system may be of the type having a pump body and a piston housed in an elastic bottle. For each pump, relative movements between the piston and the pump body causes changes in the relative-displacement between the piston and the pump body such that medicinal liquid is initially loaded into a medicine-holding cavity within the pump and subsequently dispensed.

12 Claims, 3 Drawing Sheets

DOUBLE DISPENSER FOR MEDICINAL LIQUIDS

FIELD OF THE INVENTION

The present invention relates to a double dispenser for medicinal liquids.

BACKGROUND OF THE INVENTION

Topical instillation has been the most common method of administration for ophthalmic medications since ocular treatments have existed. That is why it would be expected to be simple, practical and efficient.

Even though there is normally a certain number of patients who can administer their medications themselves, studies on the observance of medicinal directions show that a large number of them do not succeed in doing this. The necessity in ambulatory medicine of relying on the patient to carry out correct treatment is a factor in the non-compliance with doctors' directions and more particularly when the treatment is as difficult as in ophthalmology.

The impossibility of a patient positioning the end of the normal droppers without a mirror, or without corrective lenses when the latter are necessary for looking at oneself in a mirror, is very dangerous. There is a high risk of damaging the cornea together with a risk of contamination of the active constituent of the medication if the end of the dropper comes into contact with the conjunctiva as in the majority of cases.

Furthermore, when a drop is administered to the eye successfully despite the above difficulties, a significant loss of medication occurs by overflowing onto the face and by draining into the naso-lachrymal canal.

The distribution of the active substance in the general circulation essentially occurs by the intermediary of the naso-lachrymal canal. Its presence in the systemic circulation contributes to the appearance of serious general secondary effects following a simple ocular instillation and this has generated considerable interest in the design of various systems for the administration of active constituents which could minimize the risk of systemic toxicity.

If the liquid is trapped in the folds of the conjunctiva is included, the normal volume of tears in the eye is about 10 ml. A total volume of liquid of about 20 ml can be retained for a short time, if the eyelids are not closed again after the administration of the topical medication. When a single drop of medication is applied to the eye, normally having a volume of 30 to 60 ml, the major portion of the administered drop runs over the cheeks whilst the naso-lachrymal drainage system rapidly drains off the excess volume.

Thus, increasing the size of the drops does not increase the bioavailability. According to some authors, only 5% of the total quantity of the active ingredients in fact reach the aqueous humour.

On the contrary, the large size of the drops causes an exacerbation of corneal sensitivity which itself causes two synergic defence reflexes: the blinking of the eyes and lachrymation, the combination of these two resulting in the elimination of the major portion of the ophthalmic drop.

However, systemic absorption is proportional to the size of the drop, given that the subsequent drainage through the naso-lachrymal canal usually leads to the active constituent being absorbed into the plasma through the nasal mucosa or even to being swallowed.

When, in ophthalmology, active constituents are used which have potential systemic secondary effects, such as beta-blockers, it is important to try to limit the size of the drops in order to minimize the risk of secondary effects. For the purpose of reducing systemic absorption, it has been proposed for example to compress the nasal end of the lower eyelid for five minutes after the instillation in order to cause the occlusion of the lachrymal point. That is why it would be desirable to have a device designed to prevent systemic re-absorptions, that is to say to deliver a dose of the active product or products whose volume does not exceed the 25 ml maximum volume available in the conjunctival space.

Certain pathologies require, in a good number of cases, the combination of two active constituents. It would be desirable for the said device to be able to deliver, for example, two separate drops of 12.5 ml of two different liquids. A good number of active constituents used in ophthalmology are very difficult to combine into a single formulation. This is the case for example when it is desired to associate one hydrophilic active compound with a lipophilic active compound or two compounds with a different pH. Such a combination cannot be achieved in the same bottle without a major change in at least one formulation, leading to a significant reduction in its penetration or in its action. Furthermore, to administer two separate topical solutions results in excessive volumes and even more side effects while less active ingredient of the first drop is left as a result of the wash out by the second drop. This is especially true in ocular applications as well as for most of topical application.

This is the case, in ocular instillation for example, for a combination of dorzolamide (Trusopt) and epinephrine. The respective volumes of each of these two components administered is normally 30 ml for the former and 40 to 60 ml for the latter, which results in a minimum total volume of about 70 ml. Now, as mentioned above, the capacity of the eye is a maximum of 20 to 25 ml. That is why a combined formula of this association has been developed by the manufacturer, at the cost of major difficulties, an enormous budget and more than twelve years of development.

Furthermore, it would be desirable for the administration of the medication to take place in a part of the eye which is not very sensitive in order to avoid the reactions mentioned above. Such a low-sensitivity zone is the lower conjunctival cul-de-sac.

It would therefore be desirable to have an instillation device capable of simultaneously dispensing two separate active constituents and complying with the objectives and constraints defined above.

Such a device should preferably allow a patient to instill easily and concomitantly two separate drops of a medication by self-administration, in any environment whatsoever, whether this be at home, at work or elsewhere, without having to tilt the head backwards.

This device should be reliable and should eliminate the present risks of damaging the eye and of contaminating the contents.

Furthermore, the size of the drops thus administered should be small, so that the sum of the two drops administered does not exceed the maximum capacity of the eye, in order to control the dose of medication actually administered and to minimize the risk of systemic absorption with the potential toxicity which accompanies this.

In fields other than ophthalmology, certain pathologies also require, in a large number of cases, the association of two active ingredients. A large number of active ingredients, for example in Otorhinolaryngology, Pneumatology, Dermatology, Gynaecology, are very difficult to combine in a single formulation. This is the case for example, as mentioned above, when it is desired to associate a hydrophilic active compound with a lipophilic compound in a liquid phase when the two active compounds whose penetration and activity pH figures differ from one another. Such a combination cannot be achieved in the same bottle without a significant change in at least one formulation, which leads to a significant reduction in its penetration or its efficacy.

SUMMARY OF THE INVENTION

That is why the subject of the present application is a double dispenser for medicinal liquids, characterized in that it comprises:

an outer casing comprising at least one front opening and one rear opening, the said casing containing two individual paired jet trigger pumps, each provided with a dosing device dispensing predetermined doses, the aiming and direction of the jets projected by the said pumps through the front opening of the casing converging towards a point located beyond the front end of the casing at an angle such that the separation of the jets is predetermined, the two jets leaving the dispenser through two separate ejection orifices, a trigger device for the jets, accessible from the outside of the casing.

For the particular purpose of ophthalmic applications, a preferred dispenser of medicinal liquids according to the invention is characterized in that it comprises a protuberant finger at the front of the casing. In such a case in particular, a dispenser is preferred which is characterized in that the aiming and direction of the jets projected by the said pumps through the front opening of the casing converge towards a point located beyond the end of the finger furthest from the casing, and above the latter at an angle such that, at the level of the said end, the separation of the jets is about 3 to 5 mm.

The finger can have, for example, a length of 1 to 4 cm, but preferably of about 2 cm; its width can be for example between 2 and 30 mm, but preferably between 8 and 15 mm. It can be fixed, but is preferably retractable, foldable, or detachable.

This finger, when it is intended to come into contact with the base of the lower eyelid, and to pull the latter downwards, will advantageously be made with or covered with a flexible, non-harmful and preferably non-slip material such as a natural rubber-based material like latex or a synthetic material like an elastomer. The finger is located at the front of the device, the front by definition being the side through which an ocular liquid emerges in order to be administered. The finger can have various shapes according to the envisaged use, taking account of the fact that its function is to separate the dispenser from the place of application of the active constituents.

The individual pumps are of any known type, particularly of the bellows or piston type and preferably of the type requiring preliminary priming and, for example, of the type described in the U.S. Pat. No. 5,267,986, capable of ejecting a predetermined volume. A single pump, such as the one described, in double configuration, in the U.S. Pat. No. 5,320,845 and allowing the administration, if desired, of a volume of about 10 ml can also be used, even though it does not have a preliminary priming device. In fact such a pump allows the projection of an active constituent without preservative. An adapted pump is also and preferably a pump of the type described in FR-94.11785.

Such pumps are particularly suitable for sterile preparations such as ophthalmic liquids or gels. In the following text the term "liquid" indifferently refers to either of these consistencies unless otherwise mentioned.

The pumps are primed preferably by pressing the rear of the casing, if it is considered that the front part of the device according to the invention is that through which the jets emerge or that comprising the finger, and that the finger is therefore consequently located in the lower part of the casing. They can also be primed laterally.

They can be primed simultaneously or separately, the triggering of the jets however being simultaneous. Because of this, they are provided with a common triggering device. If only one of the pumps is primed, then of course only one single jet will be triggered. As a safety measure, if it is desired to impose a triggering of both jets, it is possible to ensure that the two pumps necessarily have to be primed together, for example with the assistance of a twin priming device.

For the purpose of priming and triggering them, the pumps are advantageously contained in rigid cases comprising lateral notches in particular.

The unit pumps used will preferably have, each time they are triggered, an ejection volume of less than 20 ml, generally less than 15 ml, and more particularly of between 7 and 12.5 ml, the sum of the ejected volumes preferably being less than about 30 ml and more particularly about 25 ml. Small doses can however also be administered in particular by using a pump such as described in FR-94 11785 and hereafter.

Because of the particular installation of the pumps in their casing, when the finger is applied to the base of an eyelid and the latter is pulled down in order to reveal the lower conjunctival cul-de-sac, when the pumps are triggered, the liquid is ejected into this cul-de-sac as two jets separated by a few millimeters from one another, preferably by about 10 mm.

According to the invention, the pump heads are oriented such that their jets converge. The entire pump can have such an orientation, in which case the pumps form a "V". In another embodiment, only the pump heads may have this orientation, the pump bodies being parallel, which allows a reduction in the maximum width of the device.

The device for triggering the pumps causing the ejection of the ophthalmic liquid is of any known type, with a trigger, push-button, . . . . It can be separate on each pump but, for the reasons mentioned above, this device is advantageously one which acts simultaneously on both pumps. In particular it can be located above or below the casing and preferably above so that, for example, the movement of the finger in the case of a push-button, contributes to pulling down the eyelid at the same time.

In a preferred embodiment, the device for triggering the jets is a push-button which is accessible from the outside of the casing and comprising two tongues free at their ends furthest from the button, preferably parallel, provided with two wings perpendicular to these tongues. These wings can then cooperate at their free ends, in order to trigger the jets, with a V-shaped slot formed in the opposite wall of the casing in order to cause the bringing together of the tongues and the release of the wings from lateral notches formed in rigid cases containing the pumps.

In a particularly preferred embodiment of a dispenser according to the invention, the pumps comprise three parts, namely a pump body, a piston and an elastic bottle housing them, the pump body having a front end nearest the outlet of the pump, the said front end comprising an outlet orifice obturated by an elastic membrane constituting the front of the bottle and continuing towards the rear via a pump pipe provided with a lateral fluid-inlet orifice, the piston being installed in the said pump body, the relative displacement of the end of the piston with respect to the pump body between the inlet orifice and a stop position situated near the outlet orifice thus determining the quantity of fluid expelled during the relative displacement between the piston and the pump body.

In other preferred embodiments, the bottle comprises a first bellows section having sufficient thickness to form an acceptable return means and a second bellows section, the piston comprising a rear ring locked between the two bellows sections, and the pump body being cylindrical and comprising a frontal ring, firmly attached to the front of the bottle, and a rear ring, firmly attached to the rear of the bottle behind the bellows section.

In a device according to the invention, the finger makes it possible, in ophthalmology, to simultaneously pull down the eyelid and to expose a zone which is not very sensitive and which has a good absorption capacity, namely the lower conjunctival cul-de-sac behind the lower eyelid, and furthermore it makes it possible to prevent the end of the bottle in which the product is actually contained from touching the eye and thus avoids any contamination of this recipient.

Because of its combined synergic action with the finger as described above, the application of the upper section of the casing against the eyebrow makes it possible for the principal axis of the device according to the invention to be aligned with the revealed conjunctival cul-de-sac and thus allows two separate jets to be propelled exactly into the conjunctival cul-de-sac thus exposed. That is why it is preferable for the upper front section of the casing to have a curved shape, closely following the arch of the eyebrow and the said upper section of the casing, the end of the finger and the projection axes of the pumps to be arranged such that the jets are directed preferably towards the conjunctival cul-de-sac by the downward pulling of the lower eyelid and are separated by 2 to 6 mm at the level of the point of impact of the jets on the mucosa of the conjunctival cul-de-sac. Other conformations allowing good aiming can of course be produced. Instead of placing the upper section of the casing in contact with the eyebrow, the patient can also interpose a finger, or there can be an articulated cap for exposing the pump nozzles and then it is this cap in its open position which is applied against the eyebrows.

The pumps which, in consideration of the ejected volume, can be called micro-pumps, project their respective contents into the everted cul-de-sac. This makes the following possible:

on the one hand, because of the low volume of the combined drops dispensed by the pumps, avoidance of blinking of the eyes, lachrymation, and overflow onto the cheeks, on the other hand, given that the liquid is projected, it is not necessary to tilt the head backwards.

A predetermined and constant drop volume of ophthalmic liquid is thus obtained; for the first time in ophthalmology, a liquid volume of about 15 ml or less, can ensure better ocular penetration thus resulting in increased efficiency, elimination of most of the systemic resorption and effective dispensing of two drops simultaneously into the eye without overflowing out of the eye or through the lachrymal ducts.

The pumps used are advantageously pumps provided with a one way valve.

The use of a casing and a single triggering device, combined with a priming of the pumps, allows the administration of the liquid simply by pressing the trigger, after the patient has pulled down his lower eyelid using the finger.

The device according to the present invention provides the patient with many advantages. Thus he no longer has to administer two different drops with an interval of several minutes between them and with the risk of forgetting the second one. Since the liquid is expelled by pumps, there is no longer the need, in ophthalmology, to tilt the head backwards in order to administer the product.

Administration in ophthalmology no longer provokes tearing nor overflowing of the liquid over the cheeks.

The patient has no discomfort in his ophthalmological treatment since the point at which the liquids are administered is a low-sensitivity zone and there is no longer any necessity for a mirror or of another person to administer his medication for him.

The improvements from the pharmacological point of view are also remarkable. Better ocular penetration is ensured by the small size of the drops projected into the conjunctival cul-de-sac, which does not stimulate the sensitive nerves of the cornea. Because of this, there is no blinking of the eyes nor any lachrymation reflex able to wash out the active constituent and eliminate it from this low-sensitivity zone.

The conjunctival cul-de-sac where the products are administered is a zone where there is low tear replacement, given that normally the lower eyelid does not blink. The delivery of the liquid into this specific zone increases the time of residence of the active constituent in the conjunctival cul-de-sac.

Two separate micro-drops, separately and simultaneously administered specifically into the conjunctival cul-de-sac are also more efficient than a combined formulation of 30 to 60 ml of two different conventional ophthalmic liquids, due to the respect for the specific pH figures of the two formulations and due to the total volume administered which is impossible to obtain solely by weight and surface tension as with droppers of the prior art.

The dispensing of small drops into the conjunctival cul-de-sac does not expose the cornea to any possible contact with the active constituents.

Droppers of the prior art which dispense a volume of ophthalmic liquid which is greater than the maximum volume which the front section of the eye can accept cause at least a partial immersion of the cornea, the most sensitive tissue in the human body.

Given that the drops administered with the device according to the present invention are dispensed into the low-sensitivity and low-lachrymation conjunctival cul-de-sac, even if the pH of the formulation of the active constituent is harmful to the cornea, the tolerance of these active constituents which causes red eyes must be significantly improved.

The device according to the invention also has important financial advantages. It makes it possible to reduce greatly the time necessary to obtain authorization for placing an association of different active constituents on the market in comparison with the time necessary to obtain authorization to market a combined formulation; in fact, the duration and cost of development of an association are comparable to those necessary for the development of a single original active constituent, which can be even more.

Furthermore, such a device makes the production of a combination of two different active constituents in a single formulation for ophthalmic use completely obsolete. In particular, Galenists will no longer have to carry out lengthy studies on which particular formulations could allow the combination in the same recipient of two active constituents whose active pH ranges can be different or which can have different solubilities, particularly if one of them is hydrophilous and the other is lipophilic.

The use of a system with a one way valve for the pumps allows the dispensing of formulations without preservatives, even in gel form. The device according to the invention is the only system which at present allows the dispensing of predetermined doses with a variation of less than 10%.

The device according to the invention is also extremely reliable.

The combined effects of the two active constituents will actually be obtained without having to perform two different administrations separated by a few minutes.

The device according to the invention also makes it possible to increase the topical absorption/systemic absorption therapeutic factor by simultaneously reducing the systemic resorption through the lacrimal mucosis and increasing the ophthalmological topical absorption.

The use of a flexible finger of appropriate size makes it possible to avoid any traumatism of the cornea.

When the device is used correctly, that is to say with support of the upper section of the casing, directly or with the interposition of a patient's finger, on the eyebrows and the finger of the device pulling down the lower eyelid, the drops of ophthalmic liquid are propelled exactly into the conjunctival cul-de-sac without the least contact between the end of the pumps and the conjunctiva or the cornea.

If pumps with one way valves are used, no contamination of the contents of the pumps and of the bottles is possible.

The use of an articulated cap makes it possible to prevent a bottle top from falling onto the floor or onto any septic surface before being put back into position, as for conventional bottles, thus contaminating the contents of the bottle.

Finally, the subject of the invention is also a trigger device characterized in that it comprises a push button comprising at least one tongue free at its end furthest from the button, provided with a wing perpendicular to the said tongue, capable of cooperating at its free end with the inclined wall of a cup, pressure on the button thus causing a displacement of the wing in a direction perpendicular to the direction of pushing in the push button.

If the wing, when the push button is not in its pushed-in position, is inserted in the groove of an element under mechanical tension (such as the casing of a pump as described above), then when the push-button is pressed, the wing escapes and releases the said element which can thus move longitudinally.

The above trigger device can comprise two or more tongues and wings. In the case of two tongues, the cup will be elongated in the shape of a V. In the case of three or more tongues, the cup can for example be conical.

Preferably, the elasticity of the tongues and their rigidity is sufficient for the push button to return by itself into the non-pressed position. This return can be assisted for example by means of an elastic element such as a spring situated between the button and the bottom of the cup, provided that sufficient clearance is retained for the wings to move towards the said spring in order to allow the retraction of the wings.

BRIEF DESCRIPTION OF THE DRAWINGS

The invention will be better understood by referring to the accompanying drawings in which.

DETAILED DESCRIPTION OF THE INVENTION

Figure 1:
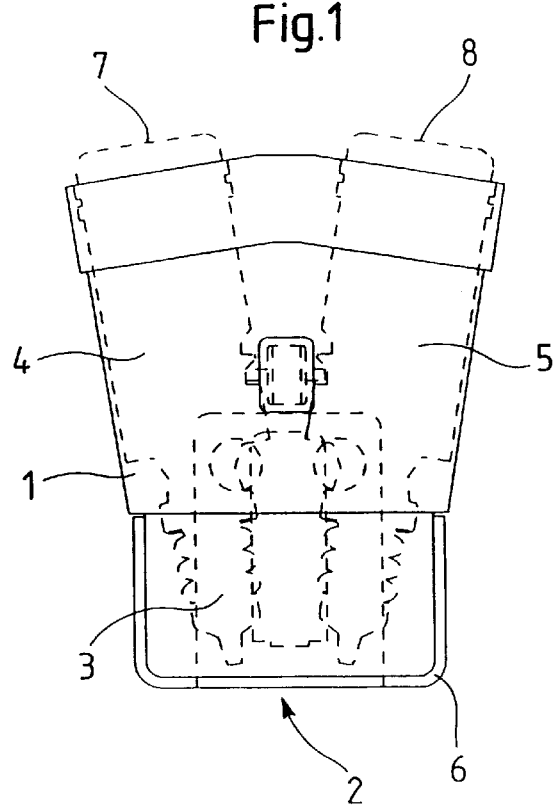
FIG. 1 is a top view of a double ocular dispenser according to the invention with the pumps in the rest state.

In FIG. 1, there can be seen the outer casing 1 comprising a wide opening 2 at the front providing free access to the heads 3 of the individual pumps 4 and 5. The lowered protective cap 6 protects and, if necessary, covers the heads 3 of the pumps 4, 5. It can be seen that the longitudinal axes of the pumps form a "V", causing the jets which the said pumps are capable of projecting to converge at a point located some distance in front of the casing. In this embodiment, the rear ends 7 and 8 of the pumps 4 and 5 located at the rear of the casing are accessible in order, for example, to be pressed with a finger in order to change to the activated setting.

In order that they may be primed simultaneously, it is possible for there to be at the rear of the casing, and for example fitted into or clipped onto the latter, a case comprising a button to be pressed and which is guided from front to back for example by slides and allowing the simultaneous activation of the two pumps; the rear ends of the two pumps are therefore pressed simultaneously by the intermediary of this button. In this way it is possible to prevent, if so desired, just one of the pumps from being primed before it is triggered.

Figure 2:
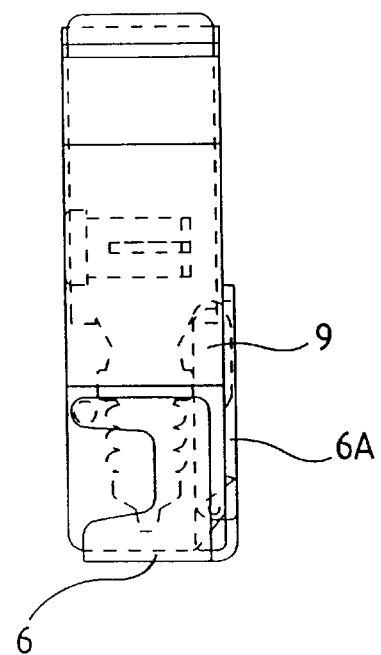
FIG. 2 is a side view of the same device, the front protective cap having been lowered and the finger in the retracted position, whilst

In FIG. 2 there can be seen, in side view, the cap for protecting the heads of the pumps 4 and 5, and the finger 9 in the folded back or retracted position. The finger 9 is hidden by a panel 6A, which is in the horizontal position in this case, which the cap comprises.

Figure 3:
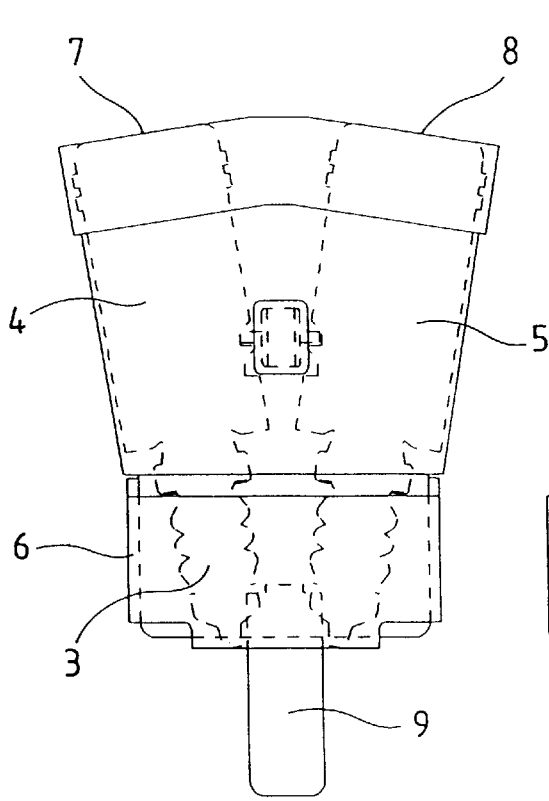
FIG. 3 and FIG. 4 are views similar to FIGS. 1 and 3 but in which the pumps are activated, the protective cap is raised and the finger is in its protuberant position.
Figure 4:
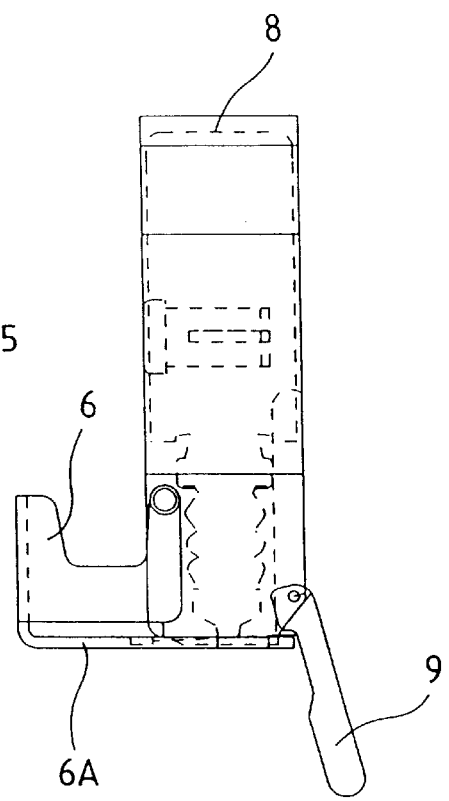

In FIGS. 3 and 4, in which the pumps are in the activated position, it can be observed that the cap 6 has been raised, releasing the finger and the heads 3 of the pumps 4 and 5 because the panel 6A comprises openings opposite the heads 3 of the pumps. The finger 9 has been unfolded in order to be able to pull down the lower eyelid. Finally, the backs 7 and 8 of the pumps 4 and 5 have both been pushed in so as to place the pumps in the activated position.

Figure 5:
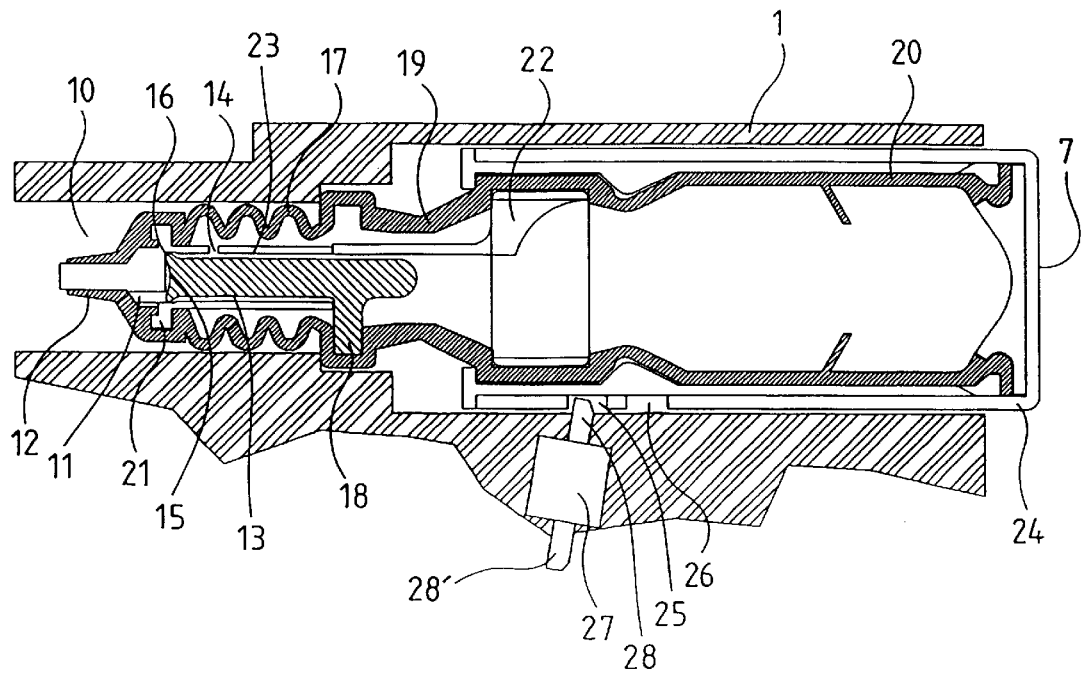
FIGS. 5 and 6 are horizontal cross-sections of FIGS. 1 and 3 showing details of an individual pump and the priming and the jet trigger device.

In FIG. 5 it is easier to observe the triggering device and a pump of the type described in FR-94.11785. The pump comprises a pump body having a forward end (or nozzle) at the end nearest the fluid outlet 10 at the front of the casing, the said forward end comprising an outlet orifice 11, obturated by an elastic membrane 12, for example made of Kraton (R) constituting the front of the bottle. The pump body continues towards the rear by a pump pipe 13 provided with a lateral fluid inlet orifice 14. This pump also comprises a mobile piston installed inside the pump body, the relative displacement of the end 15 of the piston with respect to the pump body 23 between the inlet orifice 14 and a stop position 16 located towards the outlet orifice 11 thus determining the quantity of fluid expelled during the relative displacement between the piston and the pump body. The end 15 of the piston is hermetically light-friction fitted into the pump pipe 13. The inlet orifice 14 is of the appropriate size such that only the predetermined quantity of fluid can be trapped in the end of the pump pipe 13 for the purpose of being expelled through the outlet orifice 11. The pump body and the piston are totally enclosed by the bottle 20 with the exception of the forward end, that is to say the head, of the pump body. It can be seen that the outlet orifice 11 is a channel which is axially aligned with the length of the pump. Thus the liquid is expelled along the longitudinal axis of the pump. It is observed that the pump is provided with an elastic means of returning the pump to its stop position which is constituted by the bottle itself. It should also be noted that in fact it is not the piston, locked by the ring 18, which moves but the pump body held facing the bottle 17 at the front by the ring 21 and at the rear by the ring 22. This bottle consists of a bellows section 17 which is of sufficient thickness to form an acceptable return means. On the other side of the ring 18 which the piston comprises can be seen a second elastic return means 19 constituted by a thickening of the wall also provided with a bellows-like structure. In this embodiment, the elastic membrane and the elastic bottle are formed in one piece 20. The pump body is cylindrical and here comprises a frontal ring 21 and a rear ring 22. The frontal ring 21 and the rear ring 22 are firmly attached to the ends of a bellows section of the elastic bottle by engaging in grooves in the membrane.

More particularly, the piston has an elongated shape and is provided with a plurality of anchors, that is to say radial elements, at the ends of which are arc-shaped elements constituting the rear ring of the piston 18. As has been described, the pump body 23 is cylindrical and comprises a frontal ring 21, a cylindrical rear ring 22, whose diameter is greater than that of the arcs mentioned above, the forward end of the cylindrical rear ring being recessed such that the above anchors can traverse the end of the said cylinder and thus allow, by the intermediary of grooves corresponding to the above radial elements and formed in the cylinder 23 constituting the pump body, the longitudinal displacement of the piston. Thus, when the piston withdraws, this displacement determines a cavity in which the pressure state is a partial vacuum; in fact the outlet orifice is stopped by the elastic membrane thus preventing air from entering into the pump. On further withdrawal, the piston finishes by arriving at the level of the fluid inlet orifice 14. At this time, the pump body rapidly fills with the fluid contained in the bottle 20 as will be seen in FIG. 6. The return means 19 is also compressed whilst the elastic return means 17 is in an extended position. When the ejection of the jets is triggered, at the moment the piston again arrives at the level of the fluid inlet orifice 14 (in fact it is the pump body which moves with respect to the casing whilst the piston remains locked), it traps a predetermined volume of fluid which is the volume which is ejected.

The pump is contained in a case 24 comprising two notches, 25 at the front and 26 towards the rear. In the unprimed position, a trigger is inserted in the front notch 25. In this top view, it can be seen that the trigger comprises a push button 27 provided with two wings 28 and 28' mounted on tongues with are perpendicular to the plane of the drawing. The wing 28' is intended to be inserted in notches of another case of another pump which is not shown in this figure.

Figure 6:
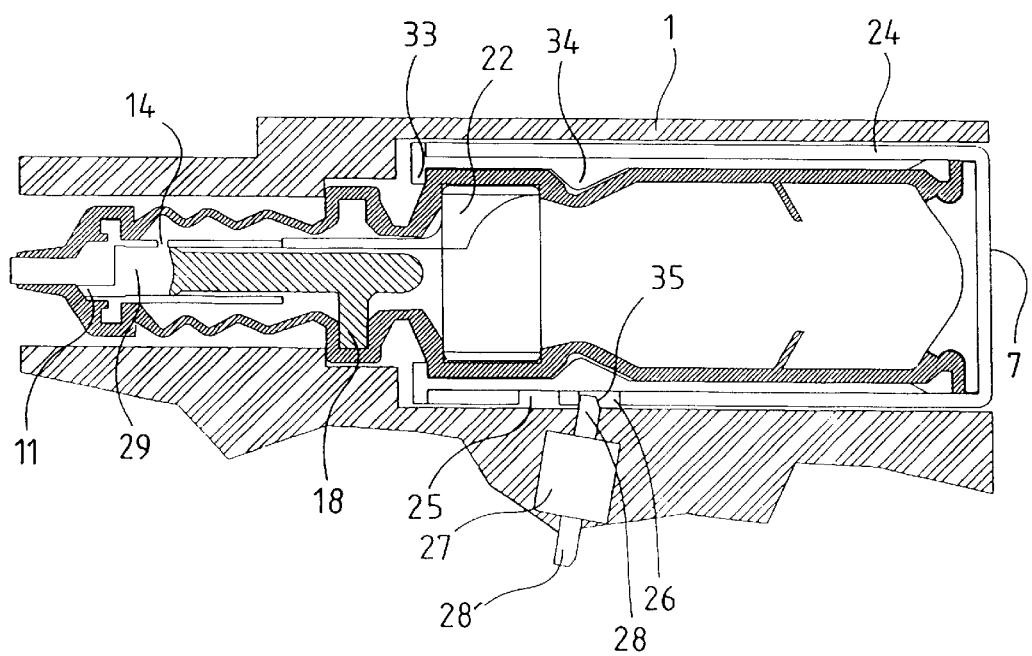

In FIG. 6 the same elements as in FIG. 5 can be seen but this time in the primed position. It can be seen that in this position, the case 24 has been advanced with respect to the casing 1. Given that the case 24 holds the rear ring 22 between a stop of the case 33 and a rib 34, and that the forward motion of the piston is blocked by the cooperation of the piston ring 18 with a narrow part at the front of the case, the pushing in by pressing on the rear end of the case containing the pump moves the pump body forwards. Because of this, a cavity 29 is formed which fills with fluid through the inlet orifice 14. The bevelled shape of the wing 28 has, due to the bevel 35, allowed the wing 28 to move from the front notch 25 into the rear notch 26, blocking the return with respect to the case. The free ends of the wings are capable of moving towards one another as will be seen below in FIGS. 7 and 8. The pump is thus in the primed position. If the trigger 27 is pressed, the wings 28 and 28' retract and allow the pump body to move towards the rear again, thus compressing the cavity 29. The pressure thus formed is imparted to the outlet orifice 11 and makes it possible to move the elastic membrane away from the end of the pump body, and thus to eject the predetermined quantity of liquid which is held in the cavity 29.

Figure 7:
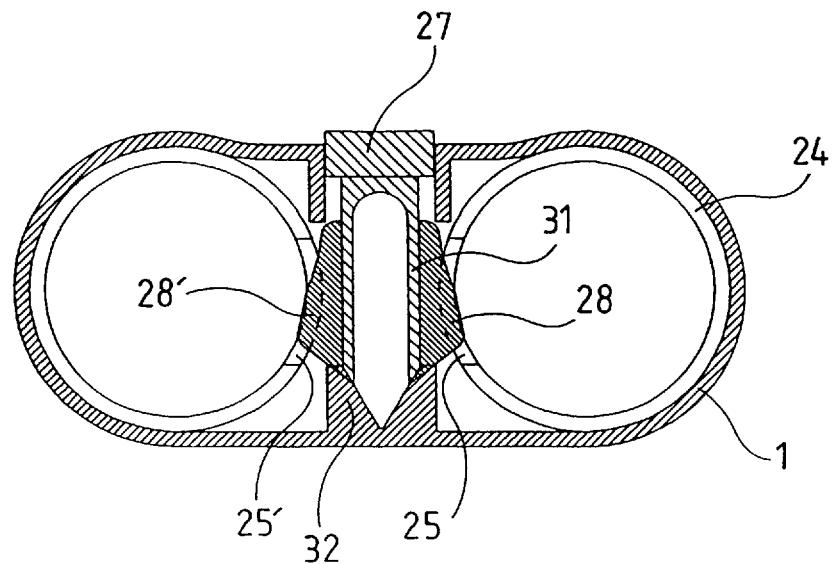
FIGS. 7 and 8 are cross-sections along AA of FIG. 1, showing details of the priming/triggering device in the active and inactive positions.
Figure 8:
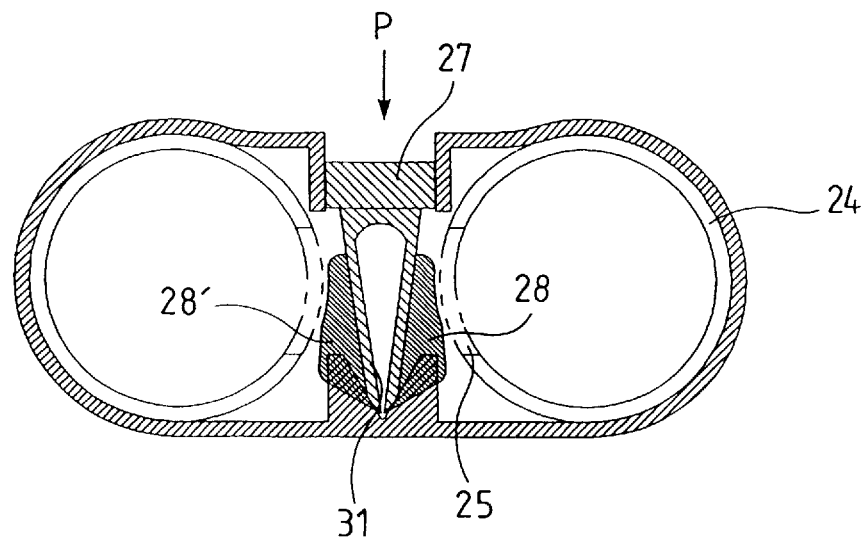

In FIG. 7, where the wings 28 and 28' are in the deployed position, it can be seen that the latter are inserted in a notch, for example 25, formed in the case 24 containing the bottle 20. These wings are located on tongues 31 which are part of the push button 27. The latter can cooperate with a V-shaped receiver 32 formed in the bottom of the casing. Thus a pressure P applied to the end of the push button 27, as seen in FIG. 8, makes it possible to bring the wings 28 and 28' towards one another and thus to retract them and release the case or cases 24, thus allowing the pumps to change position and eject the fluids.

It can be seen that the above system preserves the independence of the bottles, allowing the use of one or the other or of both of them simultaneously.

By using such a dispenser, it is possible for the first time to administer simultaneously two different products, whilst respecting their specific pH numbers both for preservation and for intra-ocular penetration.

It is also the first time that a combination can also be administered without having recourse to a synthetic reformulation in order to dispense an ocular drop. Finally it is the first time that it has been possible to administer two products having a cumulated dose of less than 25 ml.

I claim:

1. A double dispenser for medicinal liquids, comprising:

an outer casing (1) comprising at least one front opening (2) and one rear opening;

the casing containing two individual paired jet trigger pumps (4, 5), each provided with a dosing device dispensing predetermined doses, the aiming and direction of the jets projected by the pumps (4, 5) through the front opening (2) of the casing converging towards a point located beyond a front end of the casing (1) at an angle such that the separation of the jets is predetermined, the two jets leaving the dispenser through two separate ejection orifices, and at least a portion of each of the pumps (4, 5) being accessible from the exterior of the casing through said rear opening during operation of the double dispenser, wherein said at least a portion of each of the pumps is movable relative to said casing during operation of the double dispenser; and a trigger device (27) for the jets, accessible from the outside of the casing (1).

2. The dispenser according to claim 1, wherein the trigger device (27) for the projection of the jets has simultaneous action.

3. The dispenser according to claim 1, wherein axes of the heads of the pumps (4, 5) determine the direction of the jets and axes of the pumps (4, 5) are in the same plane.

4. The dispenser according to claim 1, further comprising a protuberant finger at the front of the casing (1).

5. The dispenser according to claim 4, wherein the direction of the jet projected by the pumps (4,5) through the front opening of the casing (1) converge towards a point located beyond an end of the finger furthest from the casing (1), and above the latter at an angle such that, at the level of said end, the jets are separated by about 3 to 5 mm.

6. The dispenser according to claim 1, wherein the pumps are contained in rigid cases (24) comprising lateral notches (25,26).

7. The dispenser according to claim 1, wherein the pumps are pumps which can be primed in advance.

8. The dispenser according to claim 1, wherein pump comprises a pump body, a piston and an elastic bottle housing them, the pump body having a front end nearest the outlet of the pump, said front end comprising an outlet orifice (1) obturated by an elastic membrane (12) constituting a front of the bottle and continuing towards a rear by a pump pipe (13) provided with a lateral fluid-inlet orifice (14), the piston being installed in the pump body, wherein relative displacement of an end (15) of the piston with respect to the pump body (23) between the inlet orifice and a stop position (16) situated near the outlet orifice (11) determines a quantity of fluid expelled during the relative displacement between the piston and the pump body.

9. A double dispenser for medicinal liquids, comprising:
an outer casing (1) comprising at least one front opening (2) and one rear opening;
the casing containing two individual paired jet trigger pumps (4, 5), each provided with a dosing device dispensing predetermined doses, the aiming and direction of the jets projected by the pumps (4, 5) through the front opening (2) of the casing converging towards a point located beyond a front end of the casing (1) at an angle such that the separation of the jets is predetermined, the two jets leaving the dispenser through two separate ejection orifices; and
a trigger device (27) for the jets, accessible from the outside of the casing (1);
wherein longitudinal axes of the pumps (4, 5) determine the direction of the jets.

10. A double dispenser for medicinal liquids, comprising:
an outer casing (1) comprising at least one front opening (2) and one rear opening;
the casing containing two individual paired jet trigger pumps (4, 5), each provided with a dosing device dispensing predetermined doses, the aiming and direction of the jets projected by the pumps (4, 5) through the front opening (2) of the casing converging towards a point located beyond a front end of the casing (1) at an angle such that the separation of the jets is predetermined, the two jets leaving the dispenser through two separate ejection orifices; and
a trigger device (27) for the jets, accessible from the outside of the casing (1);
wherein the trigger device (27) for the projection of the jets has simultaneous action and is a push-button comprising tongues (31) provided with two wings (28, 28') perpendicular to tongues (31).

11. The dispenser according to claim 10, wherein the tongues cooperate, at their free ends furthest from the zone at which the pressure is applied in order to trigger the jets, with a V-shaped slot formed in the casing in order to cause bringing together of the tongues (31) and release of the wings (28,28') from the lateral notches (25, 26) formed in rigid cases (24) containing the pumps.

12. A double dispenser for medicinal liquids, comprising:
an outer casing (1) comprising at least one front opening (2) and one rear opening;
the casing containing two individual paired jet trigger pumps (4, 5), each provided with a dosing device dispensing predetermined doses, the aiming and direction of the jets projected by the pumps (4, 5) through the front opening (2) of the casing converging towards a point located beyond a front end of the casing (1) at an angle such that the separation of the jets is predetermined, the two jets leaving the dispenser through two separate ejection orifices; and
a trigger device (27) for the jets, accessible from the outside of the casing (1);
wherein each pump comprises a pump body, a piston and an elastic bottle housing them, the pump body having a front end nearest the outlet of the pump, said front end comprising an outlet orifice (1) obturated by an elastic membrane (12) constituting a front of the bottle and continuing towards a rear by a pump pipe (13) provided with a lateral fluid-inlet orifice (14), the piston being installed in the pump body, wherein relative displacement of an end (15) of the piston with respect to the pump body (23) between the inlet orifice and a stop position (16) situated near the outlet orifice (11) determines a quantity of fluid expelled during the relative displacement between the piston and the pump body;
and wherein the bottle comprises a first bellows section (17) having sufficient thickness to form a return means for returning the pump body (23) from a displaced position to its ambient position and a second bellows section (19), and the piston comprises a rear ring (18) locked between the two bellows sections (17, 19), and the pump body is cylindrical and comprises a frontal ring (21), firmly attached to the front of the bottle, and a rear ring (22), firmly attached to the rear of the bottle behind the bellows section (19).

* * * * *

UNITED STATES PATENT AND TRADEMARK OFFICE
CERTIFICATE OF CORRECTION

Page 1 of 2

PATENT No. :   5,875,931

ISSUE DATE :   March 2, 1999

INVENTOR(S):   Daniel PY

It is certified that error appears in the above-identified patent and that said Letters Patent is hereby corrected as shown below:

Title page, item [57],
In the Abstract, lines 11-12, change "relative movements between the piston and the pump body causes" to --relative movements between the piston and the pump body cause --.

Column 1, line 41, change "liquid is trapped" to --liquid that is trapped --.

Column 4, line 27, change "FR-94 11785" to --FR-94.11785 --.

Column 5, line 23, change "recipient" to --receptacle--.

Column 6, line 64, change "recipient" to --receptacle --.

Column 6, line 67, change "hydrophilous" to --hydrophylic --.

Column 9, line 53, change "with are" to --which are --.

Column 10, line 67, change "jet" to --jets --.

UNITED STATES PATENT AND TRADEMARK OFFICE
CERTIFICATE OF CORRECTION

PATENT NO. : 5,875,931
DATED : March 2, 1999
INVENTOR(S) : Daniel PY

It is certified that error appears in the above-identified patent and that said Letters Patent is hereby corrected as shown below:

Column 11, line 10, change "wherein pump" to --wherein the pump --.

Signed and Sealed this

Eighth Day of February, 2000

Attest:

Q. TODD DICKINSON

Attesting Officer

Commissioner of Patents and Trademarks